United States Patent [19]
Pliquett et al.

[11] Patent Number: 5,547,467
[45] Date of Patent: Aug. 20, 1996

[54] METHOD FOR RAPID TEMPORAL CONTROL OF MOLECULAR TRANSPORT ACROSS TISSUE

[75] Inventors: Uwe Pliquett, Leipzig, Germany; Mark R. Prausnitz, Dorchester, Mass.; James C. Weaver, Sudburry, Mass.; Robert S. Langer, Newton, Mass.

[73] Assignee: Massachusettes Institute of Technology, Cambridge, Mass.

[21] Appl. No.: 96,512

[22] Filed: Jul. 23, 1993

Related U.S. Application Data

[63] Continuation-in-part of Ser. No. 705,778, May 28, 1991, abandoned, which is a continuation-in-part of Ser. No. 331,263, Mar. 30, 1989, Pat. No. 5,091,034, which is a continuation-in-part of Ser. No. 146,343, Jan. 21, 1988, abandoned.

[51] Int. Cl.$^6$ ................................................. A61M 37/00
[52] U.S. Cl. .................................... 604/20; 604/890.1
[58] Field of Search ........................... 128/632–633, 128/636–637, 760, 771; 604/20, 22, 289, 290; 601/2

[56] References Cited

U.S. PATENT DOCUMENTS

| | | | |
|---|---|---|---|
| 578,611 | 3/1897 | Rively | 604/21 |
| 3,078,850 | 2/1963 | Schein et al. | 128/419 D |
| 3,614,955 | 10/1971 | Mirowski | 128/419 D |
| 3,680,544 | 8/1972 | Shinnick et al. | 604/21 |
| 4,411,648 | 10/1983 | Davis et al. | 604/21 |
| 4,784,737 | 11/1988 | Ray et al. | 104/180.1 |
| 4,955,378 | 9/1990 | Grasso | 128/788 |
| 4,979,948 | 12/1990 | Geddes et al. | 128/786 |
| 5,007,995 | 4/1991 | Takahashi et al. | 204/299 R |
| 5,047,007 | 9/1991 | McNichols et al. | 604/20 |
| 5,098,843 | 3/1992 | Calvin | 435/287 |

OTHER PUBLICATIONS

Prausnitz, et al., "Transtissue Molecular Transport Due to Electroporation of Skin," *Electricity and Magnetism in Biology and Medicine*, 122–124 (1993).

Prausnitz, et al., "Transdermal Drug Delivery by Electroporation," *Proceed. Intern. Symp. Control. Rel. Bioact. Mater.*, 19:232–233 (1992).

Mir, et al., "Electrochemotherapy: A New Antitumor Treatment Using Electric Pulses," *Electricity and Magnetism in Biology and Medicine*, 119–121 (1993).

Mir, et al., "L'electrochimiotherapie, un Nouveau Traitement Antitumoral: Premier Essai Clinique," *C.R. Acad. Sci. Paris*, 313 Serie III: 613–618, (1991).

(List continued on next page.)

*Primary Examiner*—Michael Powell Buiz
*Assistant Examiner*—Nancy Mulcare
*Attorney, Agent, or Firm*—Hamilton, Brook, Smith & Reynolds, P.C.

[57] ABSTRACT

A method is disclosed for treating tissue in response to a stimulus generated by the tissue. In one embodiment, the method transdermally treats an organism in response to a stimulus. In this embodiment, the medication is applied to epidermis of the organism, and the epidermis is electroporated in response to a stimulus, whereby the medication passes through the epidermis at a rate sufficient to alter the stimulus, thereby transdermally treating the organism. In another embodiment, the method measures a blood component content of blood. A portion of epidermis is electroporated to cause an aqueous fluid to be directed through an electroporated epidermis to a surface of the epidermis. Thereafter, the blood component content of the aqueous fluid is measured for correlation with a known aqueous fluid blood component content associated with a known concentration of blood component in the blood. The blood component concentration of the blood can thereby be measured. In still another embodiment, the method includes directing a medication to the tissue which can alter the stimulus when the tissue is electroporated, and electroporating the tissue in response to a stimulus, whereby the medication passes through the tissue in an amount sufficient to alter the stimulus, thereby treating the organism.

5 Claims, 5 Drawing Sheets

OTHER PUBLICATIONS

Mir, et al., "Electrochemotherapy Tumor Treatment is Improved by Interleukin–2 Stimulation of the Host's Defenses," *Eur. Cytokine Netw.*, 3(3):331–334, (1992).

Belehradek, Jr. et al., "Electrochemotherapy of Spontaneous Mammary Tumours in Mice," *Eur. Cancer*, 27(1):73–76, (1991).

Okino, et al., "Optimal Electric Conditions in Electrical Impulse Chemotherapy," *Jpn. J. Cancer Res.*, 83:1095–1101, (1992).

Okino et al., "The Effects of a Single High Voltage Electrical Stimulation With an Anticancer Drug on in vivo Growing Malignant Tumors," *Jpn. J. of Surgery*, 20(2):197–204, (1990).

R. Heller, "Incorporation of Individual Cells Into Intact Tissue by Electrofusion," Electricity and Magnetism in Biology and Med., 115–117, (1993).

Heller, et al., "Development of Cell–Tissue Electrofusion for Biological Applications," *Guide to Electroporation and Electrofusion*, 393–410, (1992).

Mir et al., "Improvement of Anticancer Electrochemotherapy," *Proceedings of the American Association for Cancer Research*, 30:571, Abstract No. 2274, (1989).

Mir et al., "Pharmacological Applications of Electropermeabilization of Living Cells," Lab. de Biochimie–Enzymologie, Institute Gustave–Roussy 94805 Villejuif Cadex—France.

Mir et al., "Potentiation of Bleomycin by Local Electric Pulses: Experimental Anticancer Electrochemotherapy," *Proceedings of the American Association for Cancer Research*, 30:440, Abstract No. 2612, (1990).

Mir et al., "Electrochemotherapy Potentiation of Antitumor Effect of Bleomycin by Local Electric Pulses," *Eur. F Cancer*, 27(1):68–72 (1991).

Okino et al., "Effects of a High–Voltage Electrical Impulse and an Anticancer Drug on In Vivo Growing Tumors," *Jpn. J. Cancer Res.*, 78(12):1319–1312 (1987).

Heroux et al., "Assessment of Trauma in Tissue by Electrical Impedance Measurements." In C. T. Brighton and S. R. Pollack (Ed.), *Electromagnetics in Biology and Medicine* (SF: San Francisco Press, Inc.), pp. 215–221 (1991).

Bhatt et al., "Rhabdomyolysis Due to Pulsed Electric Fields," *Plastic and Reconstructive Surgery*, 86(1):1–11 (1990).

Heller et al., "Transfer of Human Membrane Surface Components by Incorporating Human Cells into Intact Animal Tissue by Cell Tissue Electrofusion In Vivo," *Biochimica et Biophysica Acta.*, 1024:185–188 (1990).

Titomirov et al., "In Vivo Electroporation and Stable Transformation of Skin Cells of Newborn Mice by Plasmid DNA," *Biochimica et Biophysica Acta.*, 1088:131–134 (1991).

Okino, et al., "Intracellar Bleomycin Concentration and Histrological Examination in Electrical Impulse Chemotherapy," *J. of Japan Soc. for Cancer Therapy*, 22(8):337 (1987).

Kanesada, et al., "Anticancer Effects of Electical Impulse Chemotherapy for the Primary and Metastatic Foci of Lewis Lung Carcinoma," *J. of Japan Soc. for Cancer Therapy*, 22(8):338 (1987).

Okino, et al., "Proceedings of the Japanese Cancer Association 46th Annual Meeting, Sep. 7–9, 1987," *Japan J. of Cancer Research*, 46:420 (1987).

Tatsuka et al., "An Improved Method of Electroporation for Introducing Biological Active Foreign Genes into Cultured Mammalian Cells," *Experimental Cells Research*, 178:154–162 (1988).

Melvik et al., "Increase in Cis–Dichloroldiammineplatinum (II) Cytotoxicity upon Reversible Electropermeabilization of the Plasma Membrane in Cultured Human NHIK 3025 Cells," *Eur. J. Cancer Clin. Oncol.*, 22(12):1530 (1986).

Kubota, et al., "Toxicity and Metabolism of Ara–CTP Injected into Cells by Electroporation," *Proc. Amer. Assoc. Cancer Res.*, 31:397, Abstract 2356, (1990).

Duvanel et al., "New Technique to Perform Local Anesthesia: Pulsed Iontophoresis," *Dermatology*, 177(1):30 (1988).

Orlowski et al., "Transient Electropermeabilization of Cells in Culture: Increase of the Cytotoxicity of Anticancer Drugs," *Biochem. Pharmacol.*, 37(24):4727–4733 (1988).

Tovar et al., "Electroporation and Recovery of Cardiac Cell Membrane with Rectangular Voltage Pulses," *Am. J. Physiol.* 263 (Heart Circ. Physiol. 32):H1128–H1136 (1992).

Grasso et al., "Electrofusion of Individual Animal Cells Directly to Intact Corneal Epithelial Tissue," *Biochimica et Biophysica Acta*, 980:9–14 (1989).

METHOD FOR RAPID TEMPORAL CONTROL OF MOLECULAR TRANSPORT ACROSS TISSUE

RELATED APPLICATIONS

This is a continuation-in-part application of U.S. Ser. No. 07/705,778, filed May 28, 1991, now abandoned which is a continuation-in-part of U.S. Ser. No. 07/331,263, filed Mar. 30, 1989, now U.S. Pat. No. 5,091,034, which is a continuation-in-part of U.S. Ser. No. 07/146,343, filed Jan. 21, 1988, now abandoned, the teachings of all of which are incorporated by reference.

BACKGROUND OF THE INVENTION

Many drugs and chemical agents are known to be effective in treatment of diseases. However, such agents also often have deleterious side effects when introduced into the organism in sufficient dosage to treat the targeted tissue.

One attempt to selectively treat diseased tissue is development of chemical agents which selectively affect only the diseased tissue. However, such chemical agents typically are only partially selective for the diseased tissue and often have a deleterious effect on healthy cells. Another attempt to selectively treat diseased tissue is to inject the chemical agent directly into the diseased tissue mass. However, the effect of chemical agents on diseased tissue is often dependent upon delivery of the chemical agent across cell membranes of the cells in the tissue mass as opposed to simply injecting the chemical agent into the tissue. Further, chemical agents which are injected into diseased tissue typically enter the bloodstream and are transported away from the targeted tissue mass before they have a significant therapeutic effect on the tissue mass into which they were injected.

In addition, some diseases and many injuries require very rapid and controlled responses of medication dosage to effectively suppress deleterious effects and symptoms. For example, the blood glucose level of diabetics is subject to rapid and wide fluctuation which can only be dampened by selective injections of insulin. Similarly, patients who have sustained serious injury, such as burn victims, require large doses of pain-relief medication. However, indiscriminant use of powerful analgesics can cause dangerous side-effects or even death.

In both of these examples, current methods are slow to respond to the conditions, or stimuli, which prompt treatment. With respect to diabetes, patients must independently measure blood glucose level if there is doubt as to whether an insulin injection is appropriate. Patients who suffer periods of acute pain must wait for oral medication to take effect, or be injected with large doses of potentially harmful drugs.

Therefore, a need exists for a new method for responding to stimuli generated by disease or injury.

SUMMARY OF THE INVENTION

The present invention relates to a new method for treating tissue or an organism in response to a stimulus, and to a new method for measuring the concentration of blood components.

In one embodiment, the method includes applying medication to epidermis of an organism. The epidermis is electroporated in response to a stimulus, whereby the medication passes through the epidermis at a rate sufficient to alter the stimulus, thereby transdermally treating the organism.

The method for measuring blood components includes electroporating a portion of epidermis to cause aqueous fluid to be directed through the electroporated epidermis to a surface of the epidermis. The blood component of the aqueous fluid is measured for correlation with a known aqueous fluid blood component content associated with known concentration of blood component in the blood, thereby measuring the blood component concentration of the blood.

In still another embodiment, the method includes directing a medication to the tissue which can alter the stimulus when the tissue is electroporated. The tissue is electroporated in response to the stimulus, whereby the medication passes through the tissue in an amount sufficient to alter said stimulus, thereby treating the organism.

Among the many advantages of this invention is rapid temporal control of molecular transport across tissue, such as epidermis. For example, stimuli, such as pain, can be rapidly and selectively reduced by transdermal delivery or direct delivery of an analgesic through electroporated tissue. Further, rapid therapeutic response to conditions, such as high blood glucose concentrations, can be achieved by essentially instantaneous measurement of blood component concentrations requiring control.

DETAILED DESCRIPTION OF THE INVENTION

Figure 1:
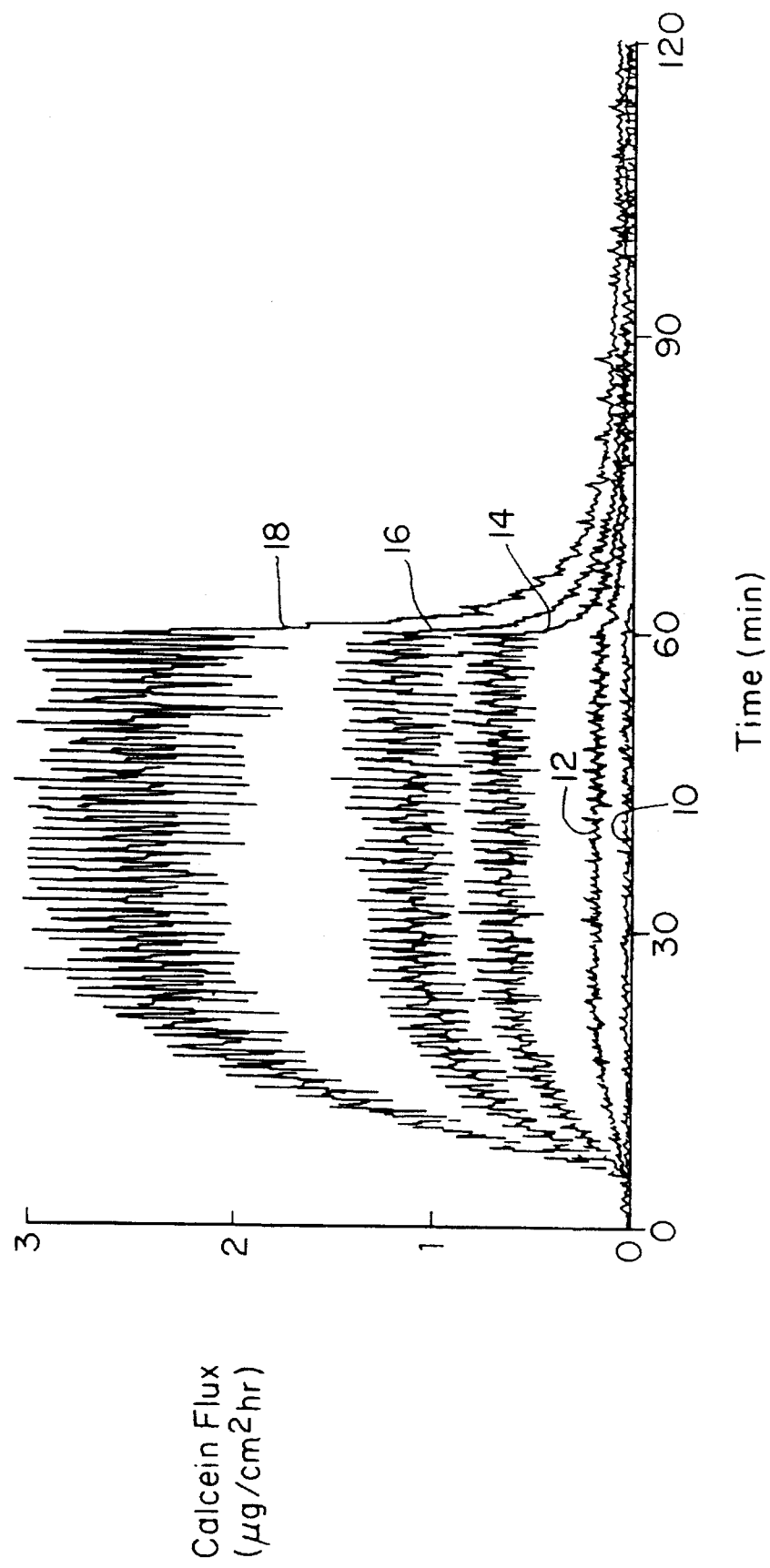
FIG. 1 shows plots of calcein flux across tissue in vitro during pulsed application of various voltages to electroporate the tissue.

The features and other details of the method of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Generally, electroporation is a method of increasing the permeability of tissue and cell membranes. The increased permeability allows transport, or migration, of chemical agents through the tissue or across cell membranes into cells. For example, electroporation can include applying a voltage across tissue in vitro to cause the permeability of the tissue and cell membranes of cells in the tissue to increase. If the tissue is in the presence of a suitable chemical agent, the chemical agent can then migrate across the tissue or into cells of the tissue. Electroporation has also been used to deliver drugs to tissue, in vivo, by applying electrodes to the surface of an organism and applying a voltage between the electrodes which exposes the tissue to an electric field. The tissue thereby becomes electroporated and allows delivery of a chemical agent, such as a drug, which has been applied either topically to the organism or injected into the blood stream of the organism, across the electroporated tissue and into cells of the electroporated tissue.

"Electroporation," as that term is used herein, means increased permeability, of a cell membrane and/or at least a portion of cells of a targeted tissue, to a chemical agent, wherein the increased permeability is caused by application of voltage across the cell or at least a portion of the tissue. The chemical agent can thereby migrate into or across the electroporated tissue, and/or across the cell membrane and into the cell. Electroporation can include, for example, killing at least a portion of the cells of targeted tissue to thereby cause the permeability of the tissue to significantly increase.

Examples of suitable apparatus and operation of the apparatus are disclosed in U.S. Ser. No. 07/705,778, filed May 28, 1991 and in U.S. Pat. No. 5,091,034, issued May 28, 1991, the teachings of which are incorporated by reference. For example, electric pulses generated by suitable apparatus to cause electroporation in the method of the invention typically are exponential pulses having a time constant in the range of between about 0.1 and about one millisecond and an amplitude in the range of between about one hundred and about one thousand volts. However, the pulse configuration can also be square, bipolar, etc. Generally, the number of pulses sufficient to cause electroporation is in the range of between about one and about ten, wherein the interval between pulses is in the range of between about 0.01 and one second.

In one embodiment, the method transdermally treats an organism in response to a stimulus. The method includes applying a suitable medication to epidermis of the organism. The medication can be applied to the epidermis before a stimulus, such as pain, occurs. An example of a suitable medication is an analgesic, such as aspirin. The epidermis is electroporated in response to a stimulus, whereby the medication passes through the epidermis at a rate which is sufficient to alter the stimulus, thereby transdermally treating the organism. In a specific embodiment, the medication can reduce the stimulus by treating tissue associated with generating the stimulus. The treated tissue can be the tissue generating the stimulus or tissue which is distinct from tissue generating the stimulus.

Also, electroporation response to the stimulus can be volitional, such as a patient initiates electroporation and consequent delivery of an analgesic to his blood stream in order to control pain. Also, electroporation can be initiated when the stimulus passes a threshold value. For example, the stimulus could be muscle contraction and the threshold value could be spasm of the muscle. Electroporation of the muscle in spasm would cause a sufficient amount of medication to treat the muscle to relieve the spasm, thereby altering the stimulus across the threshold value. The amount of electroporation can be sufficient to cause the threshold value to be passed in less than about ten minutes, or even less than about one minute.

In another embodiment, the invention includes measuring a blood component content of blood. The method includes electroporating a portion of epidermis to cause an aqueous fluid to be directed through the electroporated epidermis to a surface of the epidermis. The blood component content of the aqueous fluid is then measured. The measured blood component content can be correlated with a known aqueous fluid blood component content associated with a known concentration of blood component in the blood, thereby measuring the blood component concentration of the blood. In one embodiment, the electroporation is sufficient to cause at least about one milliliter of aqueous fluid to be directed to the epidermis surface. Also, the amount of electroporation can be sufficient to cause the aqueous fluid to collect on the surface of the epidermis in less than about ten minutes, or even less than about one minute.

An example of a suitable blood component is glucose. In a specific application of this embodiment, a patient, such as a diabetic, could employ this method to regulate insulin injections. In this specific embodiment, the blood component of the aqueous fluid which would be measured would be glucose. The diabetic patient would directly measure glucose content of a blood sample and a corresponding glucose content of aqueous fluid retrieved by electroporation of epidermis. The association between blood glucose and glucose content of the aqueous fluid could calibrate subsequent measurements of glucose content of the aqueous fluid. For example, a doubling of the glucose content of aqueous fluid retrieved by electroporation following a heavy meal would indicate a doubling of a known blood glucose content previously measured by conventional means. An appropriate glucose injection could then be made on the basis of this measurement. This embodiment can also be employed to measure the content of other blood components, such as hydrogen ion concentration.

In another embodiment, the method treats an organism in response to a stimulus. The method includes directing a medication into the tissue which can alter the stimulus when the tissue is electroporated. The tissue is electroporated in response to generation of the stimulus, whereby the medication passes through pores in the tissue in an amount sufficient to alter the stimulus, thereby treating the organism. The medication can be directed to the tissue before generation of the stimulus.

An example of a suitable medication is an analgesic, such as aspirin. An example of the suitable stimulus is pain. In one embodiment, electroporation is volitional: that is, a patient can initiate electroporation to cause a suitable medication, such as an analgesic, to reduce a stimulus, such as pain. Further, tissue can be electroporated in response to stimulus which passes a threshold value, such as by exceeding, or by being reduced below, the threshold value. The threshold value can be passed in less than about ten minutes, or even less than about one minute. The tissue which is electroporated can be the same tissue, or distinct tissue from that which generates the stimulus.

The invention will now be further and specifically described by the following examples. All parts and percentages are by weight unless otherwise specified.

EXEMPLIFICATION

Materials: Phosphate-buffered saline (PBS) was prepared, containing 138 mM NaCl, 8.1 mM $Na_2HPO_4$, 2.7 mM KCl, and 1.1 mM $KH_2PO_4$ (Mallinckrodt, Paris, HY), and adjusted to pH 7.4 by adding NaOH or HCl (Mallinckrodt). Calcein was obtained from Sigma (St. Louis, Mo.).

Skin Preparation: Using established skin sample preparation methods, full thickness excised cadaver skin was obtained within 48 hrs. post mortem and stored at 4° C./95% humidity for up to 1 week. Epidermis samples were heat separated by submerging full thickness skin in 60° C. water for 2 min. and gently removing the epidermis. All samples were stores at 4° C./95% humidity for less than 3 weeks. Tissue was obtained from four sources (three local hospitals and the National Disease Research Interchange) to minimize any artifacts of tissue acquisition. Tissue was generally from the abdomen, removed just lateral to the midline, although tissue from the breast, back, and thigh have been used as well.

In Vitro Methods: Prepared skin samples were loaded into side-by-side permeation chambers, exposed to well-stirred PBS, and allowed to hydrate fully (3–18 hrs.) Fresh PBS then was added, with 1 mM calcein on the outer, stratum corneum side. Electric pulsing was applied with Ag/AgCl electrodes (In Vivo Metrics, Healdsburg, Calif.). An exponential-decay pulse ($\tau=1.1$ msec, GenePulser, Bio-Rad, Richmond, Calif.) was applied according to protocols described below with the negative electrode on the stratum corneum side. Continuous measurement of receptor compartment fluorescence was achieved by continuously pumping (at ~50 ml/min.) receptor compartment fluid to a spectrofluorimeter. Fresh PBS was pumped into the receptor compartment at the same rate to maintain a constant receptor compartment volume. The receptor compartment was well stirred. Analysis by calibrated spectrofluorimetry (Fluorolog-2, model F112A1, Spex Industries, Edison, N.J.) allowed continuous measurement of receptor compartment fluorescent compound concentrations, and thereby calculation of transdermal fluxes.

Reported voltages are transdermal values. During a pulse, the apparent resistance of the chamber, without skin (but including electrodes, saline, and interfacial resistances), was 480 ohms, independent of the pulse voltage. The apparent resistance of the chamber with skin varied from 900 ohms during lower-voltage pulses (~50 V across skin) to 600 ohms during higher-voltage pulses (~500 V across skin). Transdermal voltages were determined by calculating the ratio of the apparent skin resistance to the apparent total chamber (with skin) resistance. This ratio is equal to the ratio of the transdermal voltage to the voltage across the whole chamber (with skin). By applying a voltage pulse and measuring the resulting current, apparent resistances were calculated by dividing the applied voltage by the measured current.

Results of applying the above-described experimental procedures are described below with reference to FIGS. 1 through 5.

FIG. 1

Calcein flux was measured across tissue in vitro. Several different voltages (transdermal) were separately applied to the tissue, each application occurring over a period of an hour, wherein the frequency of pulsation was one pulse per minute and the length of each pulse was 1.1 millisecond. The various voltages applied were: 75 volts (Curve 10); 165 volts (Curve 12); 235 volts (Curve 14); 300 volts (Curve 16); and 465 volts (Curve 18). This shows the rapid onset of transport across skin when using electroporation.

FIG. 2

Figure 2:
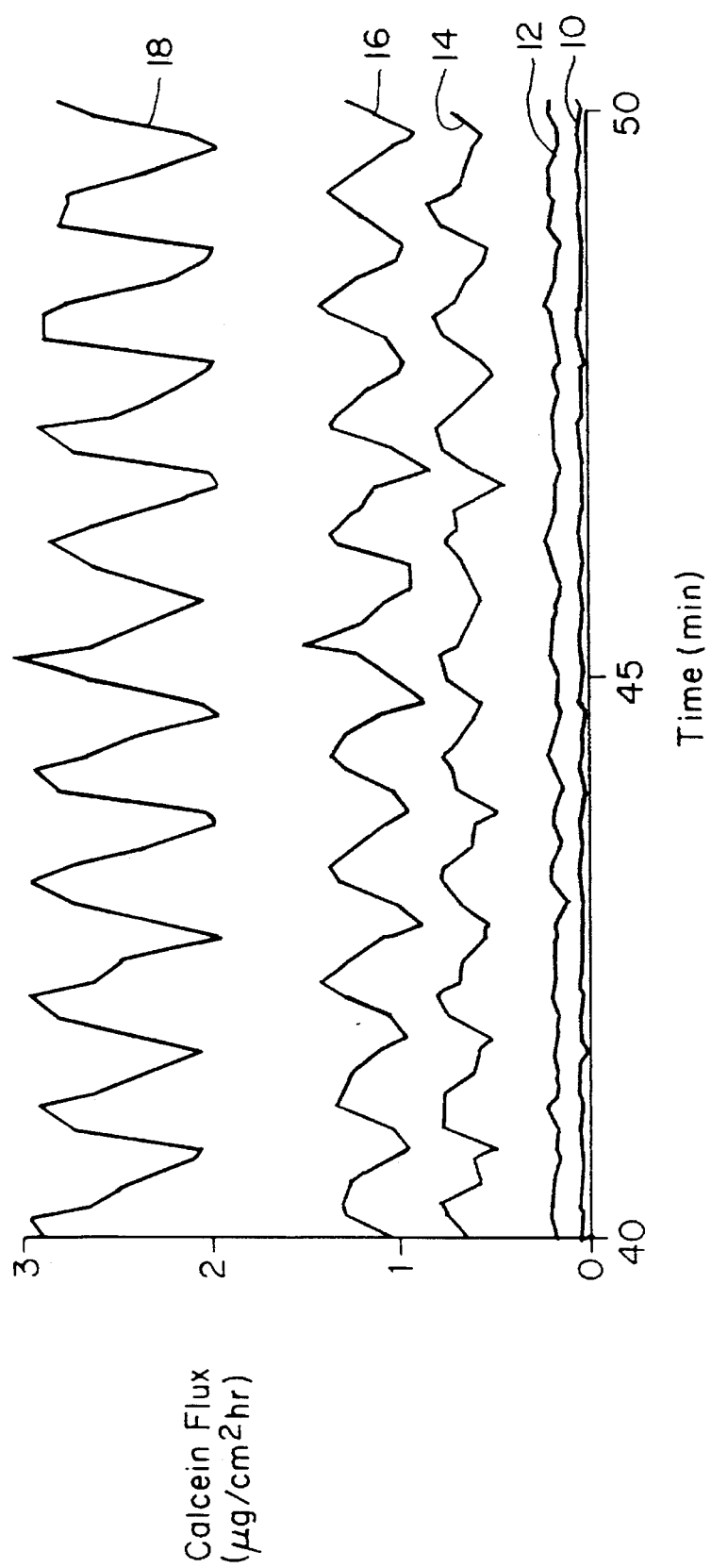
FIG. 2 shows a portion of the plots of FIG. 1 which extend from a forty minute mark to a fifty minute mark of pulsed voltage application.

An expanded view of a ten minute period, forty minute mark to a fifty minute mark, of the plots from in FIG. 1 are shown in FIG. 2. This drawing shows the changes in flux (transport) exhibited in response to individual pulses.

FIG. 3

Figure 3:
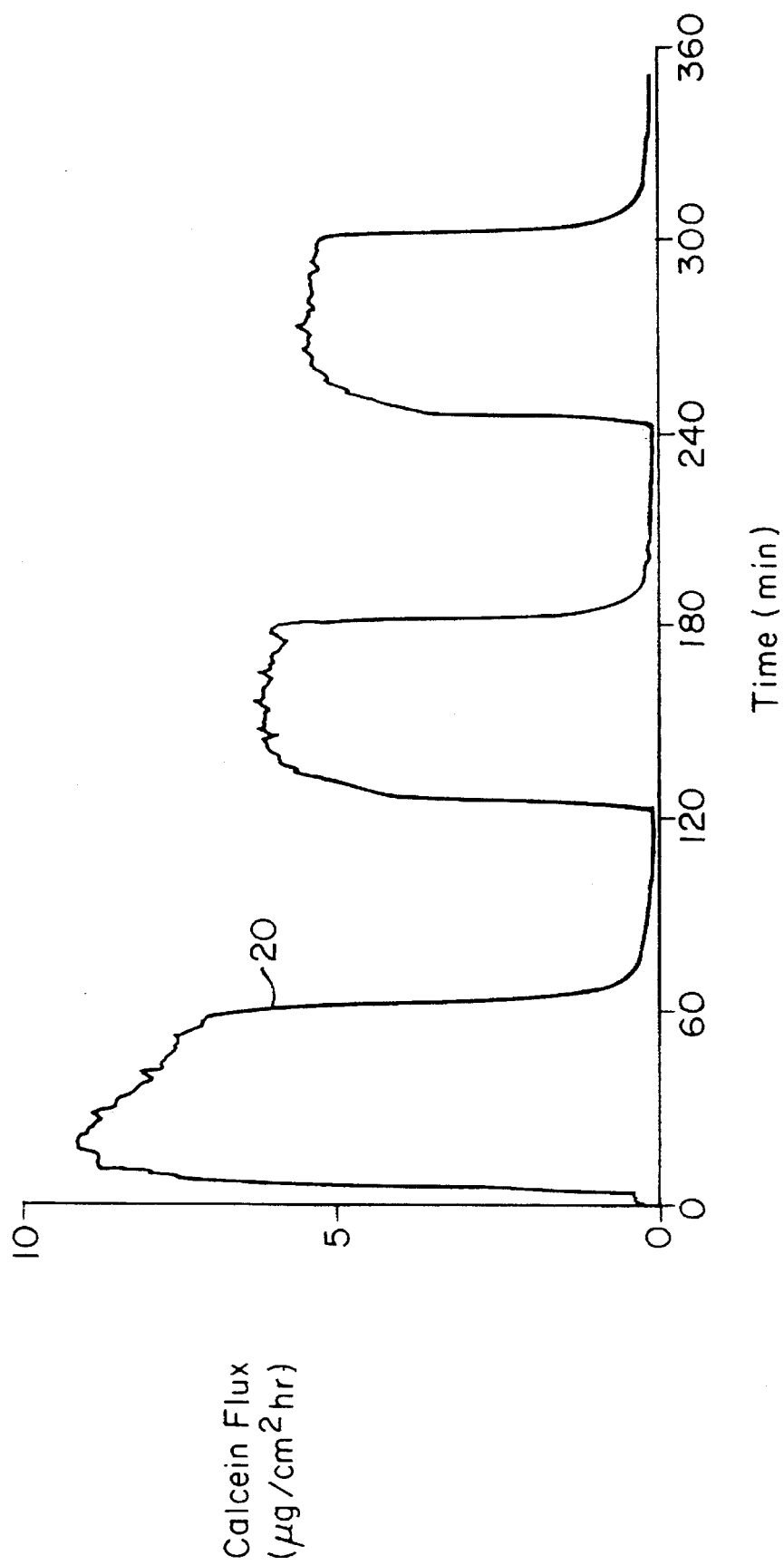
FIG. 3 is a plot of calcein flux across periods of pulsed voltage application to tissue, wherein the periods are separated by periods of equal length wherein there was no application of voltage.

Calcein flux was measured across tissue in vitro over extended periods of electroporation, followed by equal periods without electroporation. Specifically, three sixty minute periods of applying 300 volt pulses, each having a pulse length of 1.1 millisecond and at a frequency of one pulse per second, were followed by equal periods during which there was no application of voltage. Curve 20 of FIG. 3 shows that calcein flux during the period of electroporation is significantly higher (i.e. during the 1st, 3rd and 5th hour) than during the periods in between (2nd and 4th hours). This drawing shows that the rapid onset of transport can be repeatedly obtained.

FIG. 4

Figure 4:
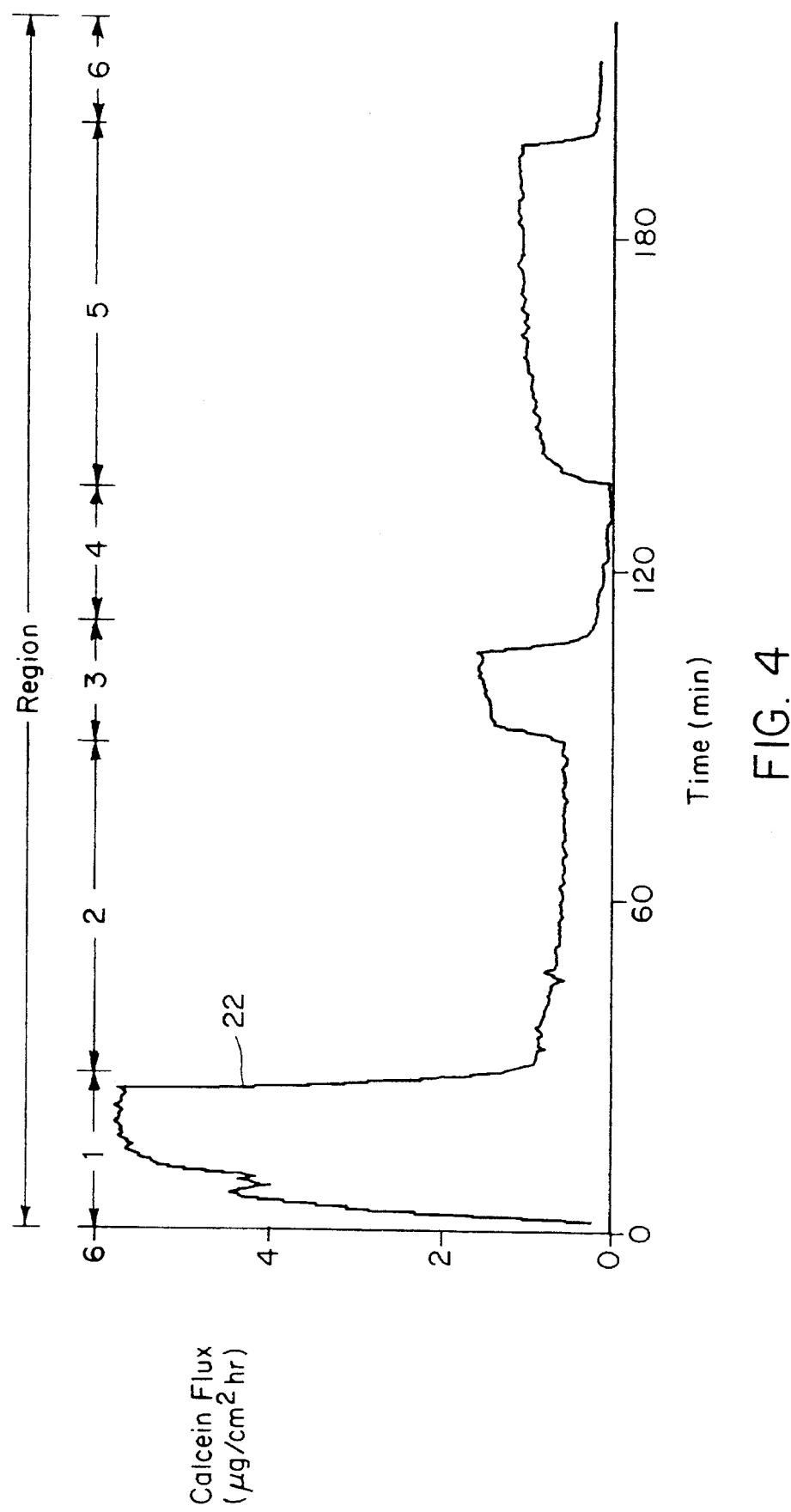
FIG. 4 is a plot of calcein flux during sequential periods of probed voltage application wherein the voltage varied but the pulse length and frequency remained constant.
Figure 5:
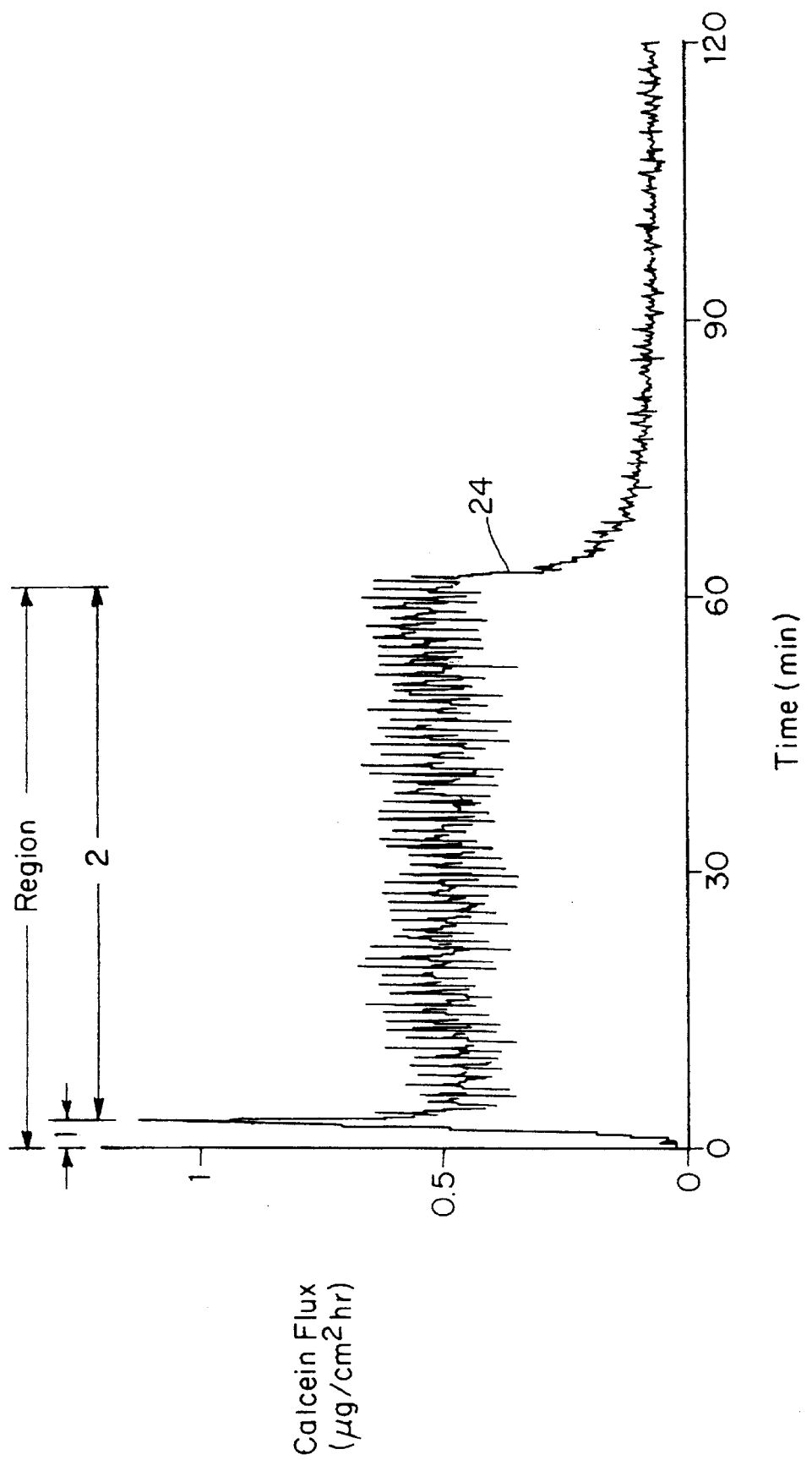
FIG. 5 is a plot of calcein flux during a short period of relatively rapid frequency of pulsed voltage application followed by a longer period of a reduced frequency of pulsed voltage application.

Various voltages were applied sequentially for extended periods of time. Region 1 of Curve 22 in FIG. 4 shows calcein flux across tissue in vitro when pulses of 465 volts, having a pulse length of 1.1 milliseconds, and a pulse frequency of one pulse per minute, is applied over a period of about 30 minutes. Region 2 shows calcein flux using 165 volt pulses of the same pulse length and frequency over the next 60 minutes. Region 3 shows calcein flux using 300 volt pulses for 15 minutes: Region 4 and 6 show calcein flux when no voltage is applied. Region 5 shows calcein flux at 235 volts over a period of one hour.

As can be seen in FIG. 4, the amount of calcein flux varies directly with the voltage applied, even when various voltages are applied in sequence to the same tissue. Further, the changes in transport rate is effected rapidly.

FIG. 5

Calcein flux across tissue in vitro is shown for 300 voH pulses having a pulse length of 1.1 milliseconds. Region 1 of Curve 24 shows calcein flux where the pulse frequency was one pulse every five seconds. Region 2 shows calcein flux when the pulse frequency was reduced to one pulse every minute. As can be seen from Curve 24, the rate of calcein flux was much greater in Region 1 than in Region 2. This drawing also shows how pulsing protocols can be altered to effect even more rapid onset of transport.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method for measuring a blood component content of blood, comprising the steps of:
   a) electroporating a portion of epidermis to cause an aqueous fluid to be directed through the electroporated epidermis to a surface of the epidermis; and
   b) measuring the blood component content of the aqueous fluid for correlation with a known aqueous fluid blood component content associated with a known concentration of blood component in the blood, thereby measuring the blood component concentration of the blood.

2. A method of claim 1 wherein the blood component is glucose.

3. A method of claim 1 wherein the blood component concentration is hydrogen ion concentration.

4. A method of claim 1 wherein the electroporation is sufficient to cause at least one milliliter of aqueous fluid to be directed through the electroporated epidermis in a period of less than about ten minutes.

5. A method of claim 4 wherein the electroporation is sufficient to cause at least one milliliter of aqueous fluid to be directed through the electroporated epidermis in a period of less than about one minute.

* * * * *

UNITED STATES PATENT AND TRADEMARK OFFICE
CERTIFICATE OF CORRECTION

| | |
|---|---|
| PATENT NO. : | 5,547,467 |
| DATED : | August 20, 1996 |
| INVENTOR(S) : | Uwe Pliquett, Mark R. Prausnitz, James C. Weaver and Robert S. Langer |

It is certified that error appears in the above-identified patent and that said Letters Patent is hereby corrected as shown below:

At column 1, before the Background of the Invention section, insert the following:

--GOVERNMENT FUNDING
      This invention was made with government support under Grant Number DAAL03-90-G-0218, awarded by the Department of the Army, and Grant Number NIH-5R01-GM34077, awarded by the National Institute of Health. The government has certain rights in this invention.--

Signed and Sealed this

Twentieth Day of October, 1998

*Attest:*

BRUCE LEHMAN

*Attesting Officer*    *Commissioner of Patents and Trademarks*